United States Patent
Howat et al.

(10) Patent No.: US 8,343,136 B2
(45) Date of Patent: Jan. 1, 2013

(54) INTRODUCER SHEATH WITH ENCAPSULATED REINFORCING MEMBER

(75) Inventors: William L. Howat, Laconia, NH (US); David Christian Lentz, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 132 days.

(21) Appl. No.: 12/198,484

(22) Filed: Aug. 26, 2008

(65) Prior Publication Data
US 2010/0057051 A1  Mar. 4, 2010

(51) Int. Cl.
*A61M 25/00* (2006.01)

(52) U.S. Cl. ........ 604/526; 604/523; 604/527; 604/525; 604/524

(58) Field of Classification Search .................. 604/523, 604/527, 525, 524, 526
See application file for complete search history.

(56) References Cited

U.S. PATENT DOCUMENTS

| | | | |
|---|---|---|---|
| 3,879,516 A | 4/1975 | Wolvek | 264/135 |
| 4,634,432 A | 1/1987 | Kocak | 604/167 |
| 4,898,591 A | 2/1990 | Jang et al. | 604/282 |
| 5,380,304 A | 1/1995 | Parker | 604/282 |
| 5,403,292 A * | 4/1995 | Ju | 604/527 |
| 5,527,292 A | 6/1996 | Adams et al. | 604/171 |
| 5,700,253 A | 12/1997 | Parker | 604/282 |
| 5,843,051 A | 12/1998 | Adams et al. | 604/280 |
| 6,306,124 B1 * | 10/2001 | Jones et al. | 604/509 |
| 6,464,632 B1 | 10/2002 | Taylor | 600/139 |
| 6,616,651 B1 | 9/2003 | Stevens | 604/524 |
| 6,652,508 B2 | 11/2003 | Griffin et al. | 604/526 |
| 6,837,890 B1 * | 1/2005 | Chludzinski et al. | 606/108 |
| 6,936,210 B2 | 8/2005 | Bartholomew | 264/294 |
| 6,939,337 B2 | 9/2005 | Parker et al. | 604/528 |
| 7,005,026 B2 | 2/2006 | Brustad et al. | 156/175 |
| 7,704,245 B2 * | 4/2010 | Dittman et al. | 604/523 |
| 2001/0034514 A1 | 10/2001 | Parker | 604/525 |
| 2004/0054349 A1 * | 3/2004 | Brightbill | 604/524 |
| 2004/0153049 A1 * | 8/2004 | Hewitt et al. | 604/527 |

FOREIGN PATENT DOCUMENTS
WO   WO 93/15785   8/1993

* cited by examiner

*Primary Examiner* — Kevin C Sirmons
*Assistant Examiner* — Brandy C Scott

(57) ABSTRACT

An introducer sheath and a method for making the sheath. The sheath includes a fluoropolymer liner having a passageway extending longitudinally therethrough. An inner jacket is positioned longitudinally over the liner, and the inner surface of the inner jacket is bonded to the outer surface of the liner. An outer jacket is positioned longitudinally over the inner jacket, and the inner surface of the outer jacket is bonded to the outer surface of the inner jacket. A reinforcing coil is encapsulated within the inner jacket and the outer jacket.

10 Claims, 2 Drawing Sheets

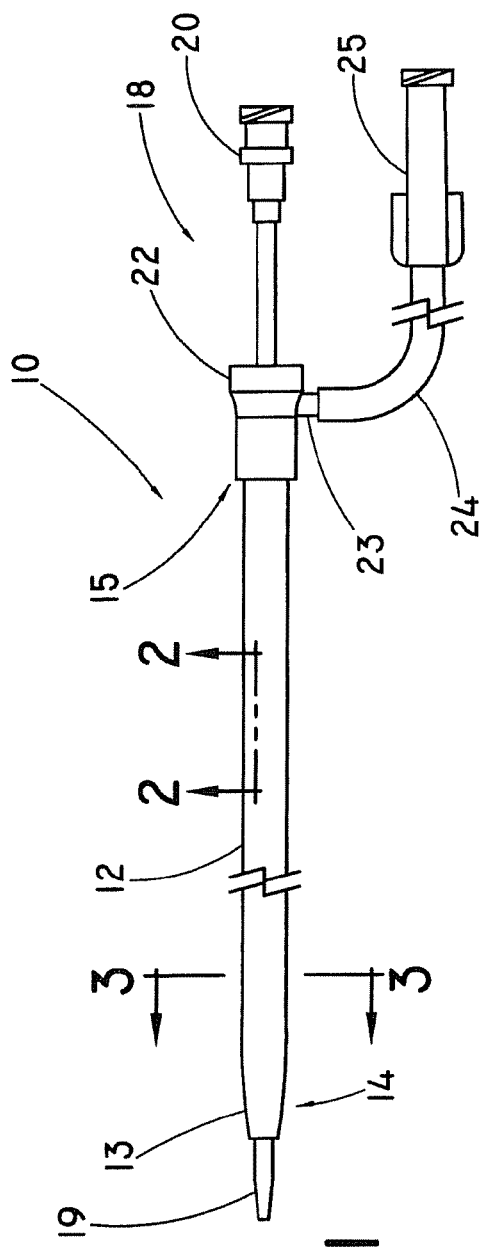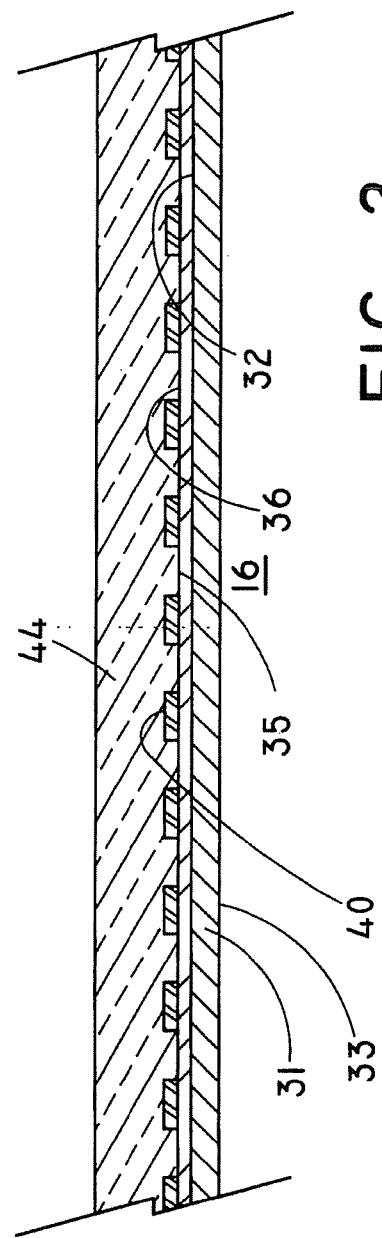
FIG. 1
FIG. 2

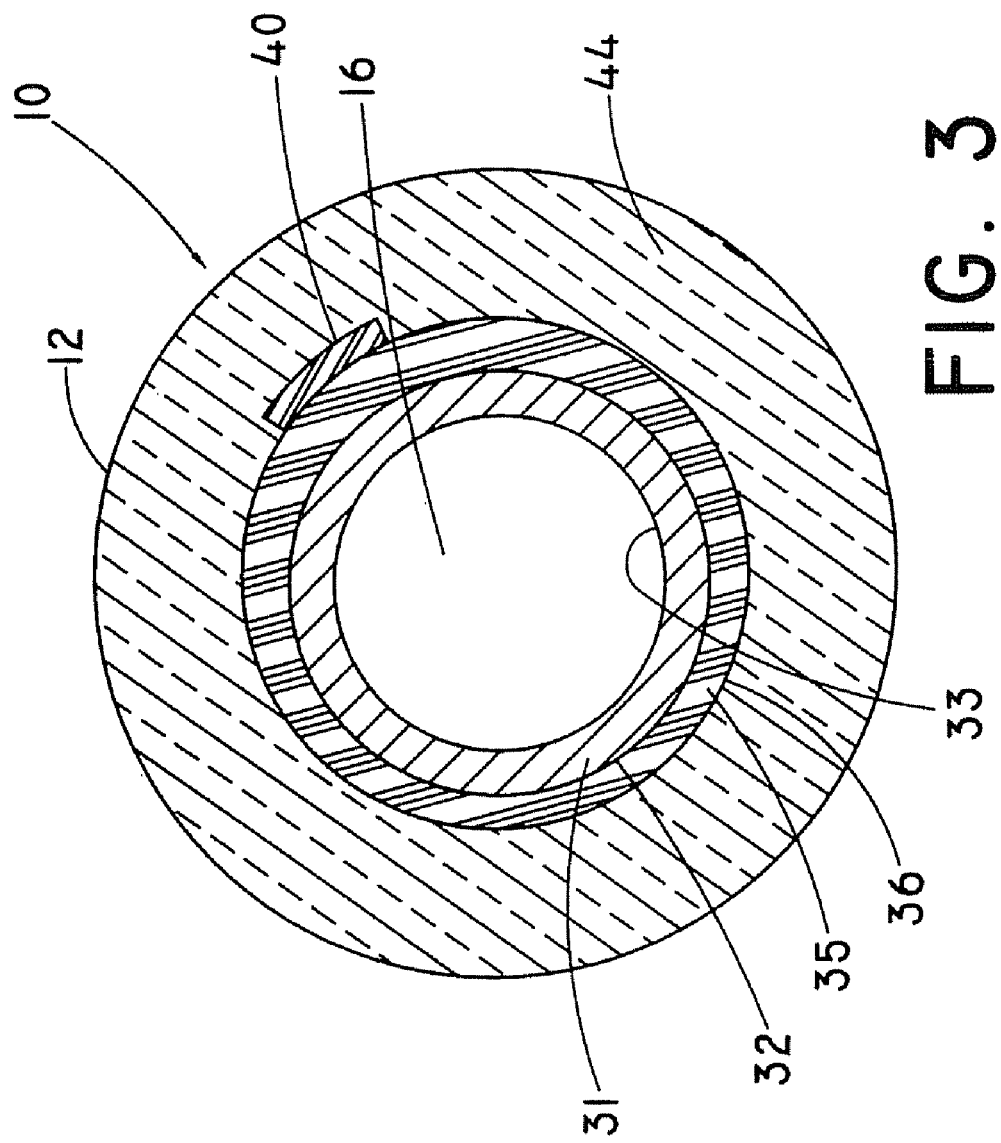

INTRODUCER SHEATH WITH ENCAPSULATED REINFORCING MEMBER

BACKGROUND

1. Technical Field

This invention relates to a medical apparatus suitable for accessing a target site within the body of a patient, and more particularly, to an introducer sheath suitable for use in introducing an interventional device into a bodily passageway of a patient.

2. Background Information

Introducer sheaths are in widespread use in the medical field for delivering a medical interventional device, such as a stent, to a target site within a bodily passageway of a patient, such as the vasculature. In order to reach the target site, the sheaths are often required to traverse tortuous pathways having sharp bends and angles. In some instances, and particularly when traversing such tortuous pathways, the sheaths exhibit a tendency to kink. Kinking reduces, and often collapses, the effective inner diameter of the sheath, thereby typically rendering the sheath unsuitable for its intended use.

The tendency of a sheath to kink is increased when the sheath is used to introduce the interventional device into one of the many smaller vessels that branch off from major vessels. In this event, the sheath may have insufficient flexibility at the very point where flexibility is most desired in order to enable proper positioning of the interventional device. In order to traverse the narrow confines of, e.g., the vascular system, the introducer sheath is typically formed of thin-wall construction. However, thin wall sheaths often have difficulty tracking narrow vessels, and exhibit an increased propensity to kink. Increasing the thickness of the sheath wall can minimally improve the level of kink resistance, as well as the trackability of the sheath. Any such increase in thickness, however, is inherently undesirable. The thickness increase limits the ability of the sheath to enter a narrow vessel, and reduces the diameter of the lumen when compared to the lumen of an otherwise similar thin-walled sheath. In addition, a larger diameter sheath necessitates the use of a larger entry opening than would otherwise be required or desirable.

One introducer sheath with improved kink resistance is disclosed in U.S. Pat. No. 5,380,304 to Parker. The introducer sheath described in the '304 patent comprises an inner liner formed of a lubricious fluoropolymer, such as polytetrafluoroethylene (PTFE). A coil is fitted around the inner PTFE liner, and an outer jacket formed of a heat-formable material, such as nylon or a polyether block amide, surrounds the inner liner and coil. The heat-formable material is heat shrunk onto the PTFE outer surface by enveloping it in a heat shrink tube, and heating the entire assembly until the material melts. As the heat-formable material melts, it flows between the spacings of the coil turns, and bonds to the outer diameter of the PTFE layer. The use of the coil in this device reinforces the sheath wall, and provides enhanced kink-resistance to an otherwise thin-walled introducer sheath.

The introducer sheath described in the '304 patent has proven to be particularly effective in delivering medical devices and medicaments to remote areas of a patient's vasculature without kinking. In order to minimize the cross-sectional profile (i.e., the outer diameter) of the sheath, the coil is generally formed of flat wire, as shown in FIG. 2 of the patent. By utilizing a flat wire coil, the sheath achieves a high level of kink resistance, and at the same time, maintains a low cross-sectional profile. The sheath described in the '304 patent enables the physician to routinely access, without kinking, target areas of the vasculature that had previously been difficult, or impossible, to reach.

With the continuous advances in the medical arts, more and more features have been developed to enhance the use of such introducer sheaths. For example, in order to improve the trackability of such sheaths, introducer sheaths have been developed wherein the proximal end of the sheath has a higher stiffness, while the distal end has a lower stiffness. One such sheath is disclosed in U.S. Patent Publication No. 2001/0034514. Since the distal portion of the sheath has a lower stiffness (and therefore is more flexible) than the proximal portion, the sheath is able to traverse portions of the anatomy that would have been difficult, if not impossible, to traverse with stiffer sheaths. Since the proximal portion has a higher stiffness (and is therefore less flexible) than the distal portion, the sheath maintains the trackability to traverse tortuous areas of the anatomy. This presence of the coil reinforcement also enables this sheath to be kink resistant through a wide range of bending angles.

U.S. Pat. No. 6,939,337 discloses a sheath having a coil reinforcement, as well as a braid reinforcement positioned over (i.e., radially outwardly of) the coil. This sheath utilizes a coil for the purposes of providing kink resistance in the same manner as the '304 patent and the patent publication recited above, and also includes a braid to enhance torqueability and pushability of the sheath. Each of the patent references cited above is incorporated herein by reference.

The improvements cited above have enabled the medical professional to more easily access areas of the vasculature that had previously been difficult, if not impossible, to reach. It is desired to continue to make advancements to enhance usage of such devices.

BRIEF SUMMARY

In one form thereof, the present invention is directed to an introducer sheath. The introducer sheath includes a liner having a passageway extending longitudinally therethrough. An inner jacket is positioned longitudinally over the liner, wherein the inner surface of the inner jacket is engaged with the outer surface of the liner. An outer jacket is positioned longitudinally over the inner jacket. The outer jacket has an inner surface bonded to the outer surface of the inner jacket. A reinforcing member is encapsulated along a length of the inner jacket and the outer jacket.

In another form thereof, the invention is directed to a method for forming an introducer sheath. An inner liner having a passageway extending therethrough is provided. A solution comprising a polymer dissolved in a solvent is applied to the outer surface of the inner liner. The solvent is evaporated, leaving a layer of the polymer on the outer surface of the inner liner, which layer comprises an inner polymer layer. A reinforcing member is positioned around the inner polymer layer, and an outer polymer layer is applied over the reinforcing member. The assembly comprising the mandrel, inner polymer layer, reinforcing member and outer polymer layer is exposed to sufficient heat to at least partially melt the inner polymer layer and outer polymer layer such that a bond is formed therebetween, and such that the reinforcing member is encapsulated within the inner and outer polymer layers.

In yet another form thereof, the invention is directed to an introducer sheath. A lubricious liner for the sheath is formed of PTFE. An inner jacket formed of a polyether block amide, nylon, or polyurethane, is positioned longitudinally over the lubricious liner. The inner surface of the inner jacket is bonded to a roughened outer surface of the liner. The inner jacket has a thickness of about 0.001 inch (0.025 mm). An outer jacket is formed of the same polymer composition as the inner jacket. The outer jacket is positioned longitudinally over the inner jacket, and bonded thereto. A flat wire coil is encapsulated in the inner jacket and the length of the outer jacket.

BRIEF DESCRIPTION OF THE DRAWINGS

FIG. 1 is a side view of a flexible, kink-resistant introducer sheath of the present invention, shown in combination with a dilator and a hub;

FIG. 2 is a longitudinal cross-sectional view of a portion of the wall of the introducer sheath of FIG. 1, taken along line 2-2; and FIG. 3 is a transverse cross-sectional view of the introducer sheath of FIG. 1 taken along line 3-3, with the dilator removed.

DETAILED DESCRIPTION OF THE DRAWINGS AND THE PRESENTLY PREFERRED EMBODIMENTS

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the inventive sheath, as well as the axial ends of various component features. The term "proximal" is used in its conventional sense to refer to the end of the apparatus (or component thereof) that is closest to the operator during use of the apparatus. The term "distal" is used in its conventional sense to refer to the end of the apparatus (or component thereof) that is initially inserted into the patient, or that is closest to the patient during use.

FIG. 1 shows an illustrative flexible introducer sheath 10 according to an embodiment of the present invention. Introducer sheath 10 includes an outer tube 12, having a distal portion 13 and a proximal portion 15. Preferably, distal portion 13 tapers to a tapered distal end 14. An inner passageway 16 (FIG. 3) extends through sheath 10 in well-known fashion.

In FIG. 1, sheath 10 is shown in combination with an optional dilator 18 and connector hub 22. Dilators and connector hubs for use with introducer devices, such as sheath 10, are well known, and the particular dilator and hub illustrated in FIG. 1 may be replaced with various other dilators and hubs known in the art. As shown herein, dilator 18 extends longitudinally through the passageway of the sheath. The dilator includes a tapered distal end 19 for accessing and dilating a vascular access site, e.g., over a wire guide (not shown) by any conventional vascular access technique, such as the well-known Seldinger technique. A Luer lock connector 20 may be attached at the proximal end of the dilator for connection to a syringe or other medical apparatus in well known fashion.

Connector hub 22 is attached about the proximal end of the sheath during use. Connector hub 22 may include one or more conventional silicone disks (not shown) for preventing the backflow of fluids therethrough. Connector hub 22 may also include a side arm 23, to which a polymeric tube 24 and a conventional connector 25 may be connected for introducing and aspirating fluids therethrough in conventional fashion.

FIG. 2 is a longitudinal cross-sectional view of a portion of the wall of introducer sheath 10 of FIG. 1. This figure illustrates the layered structure of the sheath wall. FIG. 3 is a transverse cross-sectional view of introducer sheath 10. The views of introducer sheath 10 in FIGS. 2 and 3 do not include the optional dilator 18. As illustrated, sheath 10 comprises a liner 31, having a radially outer surface 32. A thin-walled inner layer or jacket 35 shields or otherwise covers outer liner surface 32. A conventional reinforcing member, such as coil 40, is wound or otherwise fitted around the radially outer surface 36 of the thin-walled inner jacket 35. A polymeric outer layer or jacket 44 is bonded to the outer surface 36 of inner jacket 35 through the spaced turns of the coil 40.

Liner 31 is typically formed of a lubricious material. Preferably, the lubricious material comprises a fluoropolymer, such as PTFE or FEP. Lubricious liners for sheaths are well known in the medical arts, and those skilled in the art can readily select an appropriate liner for a particular use. The lubricious material provides a slippery, low friction inner surface 33 to ease insertion and/or withdrawal through passageway 16 of the dilator or medical interventional device, such as a stent. Liner 31 preferably has a substantially uniform inner diameter that extends the entire length of passageway 16, to allow passage therethrough of an interventional device having the largest possible diameter. Preferably, the radially outer surface 32 of liner 31 is roughened in any conventional manner, such as by machine grinding or chemical etching, to form an irregular surface to facilitate bonding with inner jacket 35. The wall of the liner will also preferably have sufficient structural integrity to prevent the inner jacket and/or coil turns from protruding into inner passageway 16.

Inner jacket 35 may comprise a polymeric material capable of forming a secure bond with liner 31, and more preferably, with the roughened outer surface 32 of liner 31. Preferably, the inner jacket comprises a thin layer of a polymeric material, such as a polyether block amide (PEBA), nylon, or polyurethane. The material of the inner jacket will preferably be formed from the same, or a chemically similar, polymeric material as that of the outer jacket 44, to enhance formation of a secure bond therebetween, in a manner to be described.

The coil may be formed from well-known materials for such use in the medical arts, such as a metal, a metal alloy (e.g., stainless steel or a shape memory composition such as nitinol), a multi-filar material, or a composite material. In order to minimize the cross-sectional profile (i.e., outer diameter) of the sheath, it is preferred to provide a coil with a conventional flat wire construction. However, those skilled in the art will appreciate that coil materials of other cross-sectional configurations, such as round, oval, and various other geometric configurations, may be substituted.

Outer jacket 44 may generally be formed from any composition commonly used for such purposes in a medical device. As stated, it is preferred to form outer jacket 44 from the same or a similar composition as that of inner jacket 35, e.g., a polyether block amide, nylon, or polyurethane. As a result, a very secure bond can be formed between these materials. Other outer layer compositions that are capable of securely bonding, adhering, or otherwise securely engaging the inner jacket 35 may be substituted.

One particularly preferred method of forming the inventive sheath will now be described. Initially, the liner 31 is positioned over a supporting mandrel in well-known fashion. The ends of the liner may be knotted or otherwise manipulated in a manner to prevent the solvent solution (as described hereinafter) from contacting the mandrel.

A solution of the inner jacket 35 composition dissolved in a suitable solvent is prepared for application to the outer surface 32 of liner 31. Typically, the inner jacket material is in a powdered, pelletized, or other form that promotes dissolution of the material in the solvent.

Those skilled in the art will appreciate that the inner jacket composition is soluble in many common solvents that are suitable for use herein. Preferably, phenolic solvents such as meta-cresol and cresylic acid, or various other non-polar solvents will be utilized. However, many polar solvents, such as N,N-dimethylacetamide (DMAC) and tetrahydrofuran (THF), are also generally suitable. Those skilled in the art are well aware of suitable solvents for dissolving a particular polymer, and may prefer solvents other than those specifically listed here in a particular case. Generally, a non-polar solvent is preferred for use with fluoropolymer inner jacket compositions.

Preferably, the solvent and the polymer are introduced into a suitable container, and the container is sealed. The sealed container is placed in, e.g., a barrel roller to mechanically mix the solvent and the polymer, thereby promoting dissolution of the polymer. Alternatively, other conventional mixing methods may also be appropriate, such as an ultrasonic bath. As still another alternative, the mixture may be exposed to controlled heat, with some agitation. Those skilled in the art are well aware of suitable mixing techniques, and may prefer techniques other than those specifically identified herein in a particular case.

In most cases, it is preferred to maintain the concentration of the polymer in the solvent at 10% by weight, or less. However, higher amounts (e.g., up to about 50%), may be used in a particular case. If the concentration of any particular solvent solution becomes too concentrated, the layer may be too thick to fill the etchings of the PTFE liner, thereby resulting in a bonding problem. If the solution has a low polymer concentration (e.g., less than about 5%), the resulting inner jacket layer may be too thin to accomplish the objectives of the invention.

Once the polymer is dissolved in the solvent, this solution is applied to the liner. Any conventional technique for applying a solvent solution to a substrate may typically be utilized. Preferred techniques for applying the solution to the liner include one or more of the following well-known techniques: submersion of the liner and mandrel in the solution; spraying the solution onto the outer surface of the liner; and wiping or otherwise directly coating the solution onto the outer surface of the liner. Following application of the solution to the liner by any suitable means, the solvent is evaporated away from the polymer, e.g., by air drying or by the application of heat, leaving a layer of the inner jacket polymer on the liner.

Following evaporation, the inner jacket will preferably have a wall thickness between about 0.0001 and 0.001 inch (0.0025 and 0.025 mm). Most preferably, the jacket will have a wall thickness of about 0.001 inch (0.025 mm). Those skilled in the art can readily determine an acceptable concentration level of polymer in the solvent solution, and an acceptable manner of applying the solution onto the inner liner in order to achieve the desired wall thickness without undue experimentation. Although the recited range of wall thicknesses is preferred, those skilled in the art will appreciate that wall thicknesses greater than, or less than, those specified here may be suitable in a particular case.

Those skilled in the art will appreciate that the desired wall thickness of the inner jacket may be conveniently achieved by controlling the number of repetitive immersions, sprayings, coatings, etc., as required in order to arrive at the target thickness. Although, in theory, the technique described herein can be used to prepare an inner jacket of virtually any wall thickness, it will generally be preferred in most instances to maintain the wall thickness within the optimal ranges described above, so as to not appreciably increase the outer diameter of the completed sheath.

Following application of the inner jacket 35 to the liner 31 as described, the coil 40 may be wrapped, wound, compression fitted, or otherwise applied around the outer surface 36 of inner jacket 35 in a conventional fashion. Techniques for applying a coil to a substrate in an introducer sheath are now well known, and various conventional techniques will be suitable for use herein. Non-limiting examples of such techniques are described in the incorporated-by-reference citations.

Outer jacket 44 is then applied to the outer surface of the inner jacket. Generally speaking, any conventional technique for engaging the outer jacket 44 with the inner jacket 35 may be utilized. In one preferred technique, outer jacket 44 comprises a sleeve formed of a composition that is the same or a similar composition as that of inner jacket 35, in order to promote bonding therebetween. Those skilled in the art will appreciate, however, that virtually any composition that is capable of forming a secure bond with the inner jacket material may be utilized. The sleeve is positioned over the structure comprising the coil, inner jacket, liner and the mandrel.

The entire assembly (comprising the outer sleeve, coil, inner jacket, liner and mandrel) is then placed in a heat shrink enclosure formed of a material commonly utilized for such purposes, such as fluorinated ethylene propylene (FEP). The heat shrink enclosure is then placed in an oven, and heated to a temperature (e.g., 400-500° F. (204-260° C.)) sufficient to at least partially melt the outer jacket composition and the inner jacket composition. The melted compositions flow into each other, between the turns of the coil, resulting in the formation of a secure bond between the inner jacket composition and the outer jacket composition. Additionally, melting of the inner jacket 35 enhances formation of a bond between the inner jacket and the roughened outer surface 32 of liner 31. Following formation of the bonds as described above, the assembly is allowed to cool, and thereafter removed from the heat shrink enclosure. The mandrel is then removed from the inner liner.

As illustrated in FIGS. 2 and 3, when the sheath is formed in the manner described herein, coil 40 does not directly contact the outer surface of the liner along a discrete length of the sheath. Rather, coil 40 is encapsulated within the bonded compositions that comprise inner jacket 35 and outer jacket 44. As used herein, the term "encapsulated" means that the coil is enclosed within the portion of the sheath defined by the inner jacket and the outer jacket along a length of the sheath. A minor amount of contact between the coil and the lubricious layer may be permissible in some instances, and may not appreciably detract from the objectives of the invention. However, in the most preferred embodiment the coil is completely encapsulated in the sheath portions 35, 44.

Since the inner jacket 35 directly contacts the liner 31 along its outer surface length 32, the entire length of this liner outer surface is available for bonding with the inner jacket. Accordingly, a very secure bond may be formed between the liner and the inner jacket. Since the inner jacket 35 and outer jacket 44 are formed from compositions that are readily capable of forming a secure bond therebetween, there is little likelihood of disengagement of this bond, notwithstanding the presence of the coil intermediate, or within, the respective layers.

Although the sheath described hereinabove preferably utilizes a conventional flat wire coil reinforcement, the teachings of the present invention are also applicable to sheaths or other devices having other structures disposed therewithin, such as other reinforcements. For example, in some embodiments, a braided reinforcement formed of interwoven wires may be used. Rather than having any portion of the interwoven wires in direct contact with the liner, such as the PTFE liner described herein, the wire would be positioned over an inner jacket applied over the liner as described. The outer layer then would be bonded in the manner described above, such that the wire is encapsulated in the heat shrinkable layer(s), and wherein the innermost layer bonds directly to the outer surface of the liner along the length of that liner.

Those skilled in the art will appreciate that all dimensions, compositions, etc., described herein are exemplary only, and that other appropriate dimensions, compositions, etc., may be substituted in an appropriate case. For example, other than the inner jacket described herein, the respective thicknesses of an inner liner and an outer jacket for an introducer sheath are conventional, and may be varied based upon the intended use of the sheath. If desired, the sheath can be formed to have one or more segments of varying durometer along its length, typically aligned in a sequence of decreasing durometer from the proximal end to the distal end in well-known fashion. Additionally, other features commonly found in sheaths, such as radiopaque markers, rings, coatings, etc., may also be incorporated into the inventive structure in well-known manner.

It is therefore intended that the foregoing detailed description be regarded as illustrative rather than limiting, and that it be understood that it is the following claims, including all equivalents, that are intended to define the spirit and scope of this invention.

The invention claimed is:

1. An introducer sheath comprising:
   a liner having a passageway extending longitudinally therethrough, said liner formed of a lubricious fluoropolymer and having an outer surface;
   an inner jacket formed of a polyether block amide, nylon, or polyurethane, said inner jacket positioned longitudinally over said liner, said inner jacket having an inner surface and an outer surface, said inner surface engaged with said outer surface of said liner, wherein said inner jacket has a wall thickness between about 0.0001 and 0.001 inch (0.0025 and 0.025 mm);
   an outer jacket formed of a polyether block amide, nylon, or polyurethane, said outer jacket positioned longitudinally over said inner jacket, said outer jacket having an inner surface bonded to said outer surface of said inner jacket; and
   a reinforcing member encapsulated in said inner jacket and said outer jacket.

2. The introducer sheath of claim 1, wherein said reinforcing member comprises a coil.

3. The introducer sheath of claim 2, wherein said reinforcing member comprises a flat wire coil.

4. The introducer sheath of claim 2, wherein said inner jacket extends substantially the length of said liner outer surface.

5. The introducer sheath of claim 1, wherein said inner jacket has a generally constant wall thickness of about 0.001 inch (0.025 mm) along said length.

6. The introducer sheath of claim 1, wherein said lubricious fluoropolymer comprises PTFE.

7. The introducer sheath of claim 1, wherein said inner jacket and said outer jacket are formed from the same polymer composition.

8. The introducer sheath of claim 1, wherein said outer surface of said inner liner is roughened, and said inner jacket is bonded to said roughened outer surface.

9. The introducer sheath of claim 1, wherein the reinforcing member is completely encapsulated within the inner jacket and the outer jacket.

10. An introducer sheath comprising:
   a lubricious liner formed of PTFE, said liner having a passageway extending longitudinally therethrough, said liner having a roughened outer surface;
   an inner jacket formed of a polyether block amide, nylon, or polyurethane, said inner jacket positioned longitudinally over said lubricious liner, said inner jacket having an inner surface and an outer surface, said inner surface bonded to said roughened outer surface of said liner, said inner jacket having a thickness of about 0.001 inch (0.025 mm);
   an outer jacket formed of the same composition as said inner jacket, said outer jacket positioned longitudinally over said inner jacket, said outer jacket having an inner surface bonded to said outer surface of said inner jacket; and
   a flat wire coil having a length, said flat wire coil encapsulated in said inner jacket and said outer jacket along said length.

* * * * *